United States Patent
Knight et al.

(10) Patent No.: US 7,771,398 B2
(45) Date of Patent: Aug. 10, 2010

(54) PEN SHAPED MEDICATION INJECTION DEVICES

(75) Inventors: Barry Knight, Surrey (GB); Stephen Knowles, Beaumont (GB); Venkitraman R Srinivas, Mumbai (IN); Ramesh Sesha, New Jersey, NY (US)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 1101 days.

(21) Appl. No.: 11/320,809

(22) Filed: Dec. 30, 2005

(65) Prior Publication Data

US 2006/0184117 A1 Aug. 17, 2006

Related U.S. Application Data

(60) Provisional application No. 60/644,498, filed on Jan. 18, 2005.

(51) Int. Cl.
*A61M 5/00* (2006.01)
(52) U.S. Cl. .................. 604/208; 604/207; 604/211
(58) Field of Classification Search ............ 604/135, 604/207–211
See application file for complete search history.

(56) References Cited

U.S. PATENT DOCUMENTS

| | | | | |
|---|---|---|---|---|
| 5,092,842 A | * | 3/1992 | Bechtold et al. | 604/135 |
| 5,279,585 A | * | 1/1994 | Balkwill | 604/207 |
| 5,626,566 A | * | 5/1997 | Petersen et al. | 604/208 |
| 5,674,204 A | * | 10/1997 | Chanoch | 604/211 |
| 5,921,966 A | * | 7/1999 | Bendek et al. | 604/207 |
| 6,001,089 A | * | 12/1999 | Burroughs et al. | 604/506 |
| 6,004,297 A | * | 12/1999 | Steenfeldt-Jensen et al. | 604/207 |
| 6,248,095 B1 | * | 6/2001 | Giambattista et al. | 604/207 |
| 6,277,099 B1 | * | 8/2001 | Strowe et al. | 604/207 |
| 6,663,602 B2 | * | 12/2003 | Møller | 604/211 |
| 6,899,699 B2 | * | 5/2005 | Enggaard | 604/246 |
| 6,932,794 B2 | * | 8/2005 | Giambattista et al. | 604/207 |
| 7,094,221 B2 | * | 8/2006 | Veasey et al. | 604/187 |
| 7,195,616 B2 | * | 3/2007 | Diller et al. | 604/224 |
| 7,291,132 B2 | * | 11/2007 | DeRuntz et al. | 604/207 |
| 7,361,161 B2 | * | 4/2008 | Bainton | 604/207 |
| 7,407,494 B2 | * | 8/2008 | Bostrom et al. | 604/207 |
| 2004/0260247 A1 | * | 12/2004 | Veasey et al. | 604/207 |
| 2007/0016142 A1 | * | 1/2007 | Burren et al. | 604/207 |
| 2008/0183139 A1 | * | 7/2008 | Burren et al. | 604/211 |
| 2008/0208142 A1 | * | 8/2008 | Moller | 604/208 |
| 2008/0287883 A1 | * | 11/2008 | Radmer et al. | 604/211 |
| 2008/0312605 A1 | * | 12/2008 | Saiki | 604/211 |
| 2009/0209920 A1 | * | 8/2009 | Moller et al. | 604/211 |

* cited by examiner

*Primary Examiner*—Kevin C Sirmons
*Assistant Examiner*—Andrew M Gilbert
(74) *Attorney, Agent, or Firm*—Bio Intellectual Property Services (LLC); O. M. (Sam) Zaghmout

(57) ABSTRACT

The present invention provides a delivery device comprising a fluid cartridge holder, housing and a piston drive mechanism that comprises a hollow piston rod and a drive-shaft. The hollow piston rod has an internal thread that mates with the external thread of the drive-shaft, forming a thread connection and being axially restrained in the proximal direction relative to the housing. The drive mechanism is in turn connected to the housing via a one way ratchet such that the piston rod is prevented from moving in the proximal direction.

45 Claims, 11 Drawing Sheets

A

B

C

A

B

C

PEN SHAPED MEDICATION INJECTION DEVICES

CROSS-REFERENCE TO RELATED APPLICATIONS

This application claims the benefit of U.S. Provisional Application No. U.S. 60/644498, filed on 18 Jan. 2005. The entire disclosure of this prior application is hereby incorporated by reference.

FEDERALYY SPONSORED RESEARCH

Not applicable.

SEQUENCE LISTING OR PROGRAM

Not applicable.

BACKGROUND OF THE INVENTION

1. Field of Invention

The present invention relates to delivery devices for the delivery of fluids into persons in need thereof. In particular this invention is related to devices, for the delivery of fluid medications into patients. These devices are multi-dose delivery devices, where a pre-selected quantity of fluids can be delivered into patients. The devices of the present invention have the overall shape and appearance of a pen, and hence have been described as "fluid delivery pens".

2. Background of the Invention

Delivery of fluids to persons in need thereof, is often necessary, in fixed doses, and/or at regular intervals. Patients, for instance, are often in need of regular doses of specific medications. For instance, diabetics require several doses of insulin injections during the course of the day. The required insulin regimen varies from patient to patient and depends on the type of insulin to be injected (slow, medium, fast acting, or specific combinations of these), the lifestyle of the patient, the circumstances, patient's actual medical condition etc. Hence diabetics often need to self-administer their medication, at the appropriate time, in the appropriate doses, and in places other then a health center, such as their homes, offices, restaurants etc. Thus a delivery device for use in such circumstances must be easy, convenient, as well as non-embarrassing to use, and convenient to carry around in public. Fluid delivery pens have been developed to enable such self-administration of devices.

Typically a fluid delivery pen comprises a cartridge holder into which a cartridge of fluids, such as a liquid medication, is loaded. The cartridge holder usually has an elongated tubular design, whose distal end is adapted to carry a needle assembly, such that the proximal tip of the needle, carried by the needle assembly, is in direct contact with the fluid inside the cartridge. The proximal end of the cartridge is generally closed with a plunger, whose inner surface is in contact with the fluid. The outer surface of the plunger is in turn connected to a piston rod. A measured movement of the plunger-piston rod in the distal direction results in the delivery of a measured dose of the fluid. The delivery device is calibrated such that the dose delivered is directly related to the movement of the plunger in the distal direction. In addition the delivery device comprises a dose setting means for setting the dose of the fluid to be dispensed, and a driving means for pushing the plunger through a distance determined by the dose setting means. The piston rod, dose setting means and driving means are enclosed, partly or wholly, in a housing. The distal portion of the delivery device, that carries the needle assembly, is enclosed by a cap.

The shape of the device is similar to a pen of suitable weight and length that can be carried conveniently in the pocket. Such fluid delivery devices are used by first loading the cartridge holder with the fluid containing cartridge, mounting the needle assembly, setting the appropriate dose and injecting the fluid. Such devices are described as "reusable", when an empty cartridge is replaced by a fresh one, as opposed to "disposable" ones, that come supplied with the cartridge, and is discarded once the cartridge is empty.

There can be several variations to the above general design. For instance, the needle assemble may be reusable or fixed, the dose setting device and driving means may differ in different types of devices, the dispenser may have a feature which could allow the piston rod to travel only in one direction. In addition, the devices may differ in the nature of the scales used to set dosages, and the convenience in using them.

While the devices presently available have served the general purpose as devices for the convenient self-administration of fluids, such as drugs, there is, nevertheless, ample room for improvement in the design of such delivery devices.

For instance, it would be desirable if the mechanism could accommodate both reusable and disposable feature. It would also be desirable if the working mechanism of the device is designed in a configuration that is adaptable to a range of body shapes and styles.

Additionally, it would be desirable if the device can be assembled from as few individual components as possible, and that the components are designed for fast and efficient assembly, either manual or automated.

Another desirable feature would be a device whose parts are made of plastic that can be recycled. It would be further desirable if the device is designed so that setting and injecting doses are easier for the elderly and physically challenged. This could be accomplished, for instance, by incorporating mechanisms that produce tactile and auditory "clicks" while the dose is being set—every "click" indicating a change in a unit dose setting.

Also it would be desirable to incorporate a magnifying lens to magnify the numerals on the dose dial to improve readability for the visually challenged.

It would also be desirable if the parts of the device can be designed in sub-assemblies, since this enables functional areas of the pen to be checked and tested separately, and in greater detail, before the pen is fully assembled.

Another desirable feature would be a device that has a direct mechanical drive between the person applying the injection force and the piston rod being driven forward to inject the medicament. This ensures the person is aware of any problems in the dose delivery. Mechanisms which, for instance, use a spring force to eject the dose, such as those described in U.S. patent U.S. Pat. No. 5,104,380, can occasionally deliver an incomplete dose if the force required to push the cartridge is greater then would normally be the case. It is also desirable that where a set dose can't be fully delivered, because the cartridge becomes empty, the device can indicate to the patient how much of the dose has been delivered.

It would also desirable if the delivery mechanism offers a mechanical advantage to the user to reduce the force that must be applied by the user during injection. In U.S. Pat. No. 4,973,318 for instance, the user has to depress the application knob with the same force and over the same distance as required to move the cartridge. For the smooth running of the piston drive mechanism, it is important that dirt and dust are not allowed to enter the mechanism. Many delivery mechanisms in the prior art, such as those described in U.S. patents U.S. Pat. Nos. 6,235,004, 6,004,297, 5,611,783, 6,454,746, 5,279,586 etc., have an externally exposed threaded piston rod which, in a reusable device, could be vulnerable to picking up dirt and dust thereby hindering the working mechanism. It would hence be desirable if the thread drive mechanism is enclosed and thus protected from dirt and dust when the cartridge housing is removed.

Also in reusable devices it would be desirable that the piston rod is of strong design to avoid damage when changing cartridges or resetting the mechanism. Such resetting often involves the use of a non-locking thread, and as a consequence a given diameter of the thread cannot be exceeded for any particular thread pitch. This results in many externally threaded piston rods in the prior art being of relatively small diameter, and therefore vulnerable to damage or deformation. Examples of patents with outer threaded piston rods include U.S. Pat. Nos. 6,235,004, 6,004,297, 5,611,783, 6,454,746 and 5,279,586. A piston rod that has an internal non-locking thread can be substantially larger in diameter and will have a structurally efficient hollow cross section making it substantially stronger then an equivalent externally threaded rod.

The present invention describes a fluid delivery device incorporating all the features described above. The description outlined below is for illustrative purposes and is not intended to limit scope of the invention either in its design or its application.

DETAILED DESRCRIPTION

The fluid delivery device in accordance to the present invention comprises a holder for a fluid containing cartridge, two concentrically arranged housing-tubes—inner and outer housing-tubes, and two concentrically arranged dose-drums—inner and outer dose-drums. The cartridge holder carries a fluid containing cartridge, that on its distal end carries a needle, and on its proximal end a plunger. The proximal end of the cartridge holder has an outer threading that mates with a corresponding threading on the inner-side of the distal end of the outer housing-tube, forming a self-locking mechanism.

The inner housing-tube encloses the piston drive apparatus, while two concentrically arranged dose-drums are placed between the inner and outer housing-tubes. Portions of the distal region of inner housing-tube, diametrically opposite each other, are molded as two sprung-clips that are mobile when the cartridge holder is assembled into the device. The two sprung-clips comprise an inner-toothed surface. The inner and outer housing-tubes are joined at the non-clip portions of the proximal region of the inner housing-tube and the outer housing-tube. In one embodiment, the housing-tubes are joined be means of a thread-screw connection. Alternatively, the non-clip portions of the proximal region of the inner housing-tube are welded to the inner wall of the outer housing-tube. The piston drive mechanism comprises three distinct components, a hollow piston rod, a piston rod cap that is free to rotate on a bearing surface with the piston rod, and that directly contacts the cartridge plunger, and a drive-shaft located, at least partially, inside the piston rod.

A flexible locking bush, comprising an outer tooth surface, is placed between the distal end of the piston rod and the inner housing-tube. When the cartridge housing is assembled into the pen, the two inner housing-tube sprung-clips are deflected inwards, so that the teeth on the inner side of the sprung-clip engage the outer surface teeth of the locking bush, preventing the locking bush from rotation. The inner surface of the locking bush has protrusions which mate with longitudinal channels that traverse the length of outer surface of the piston rod. Thus when the cartridge-holder is assembled into the device, the piston rod is prevented from rotating.

On the other hand when the cartridge-holder is removed, the teeth on the sprung-clips and on the locking bush are disengaged which then allows the rotation of the locking bush and the piston rod. The proximal edge of the locking bush has a ridge that locks into a corresponding groove formed beyond the proximal edge of the two sprung-clips of the inner housing-tube. The distal edge of the two sprung-clips has a raised ramp that locks into a corresponding champfer on the inner side of the proximal edge of the cartridge-holder, pushing the sprung-clips progressively inwards as the cartridge holder is screwed into the outer housing-tube. Placed between the outer and inner housing-tubes are the two concentrically arranged dose-drums.

The inner side of the outer housing-tube and the outer dose-drum have a helical track-helical rib arrangement that can form a not-self-locking connection between them. In one embodiment of the present invention, the not-self-locking thread connection is formed by a helical thread present in the outer housing-tube and that engages a helical rib/s present in the outer dose-drum. Alternatively, the helical track can be present on the outer surface of outer dose-drum, while the helical rib/s are present on the inner side of the outer housing-tube. The proximal portion of the dose-drums project out of the proximal end of the outer housing-tube, so that the proximal portion of outer dose-drum—the dose-knob—is amenable to rotation by hand. Thus when the dose-knob is rotated, it is both rotated and axially displaced relative to the housing. Depending on the orientation of the helical track, rotation of dose-knob can be either in the clockwise or in anti-clockwise direction resulting in its proximal displacement relative to the housing (viz. the "dose setting" displacement of the outer dose-drum). Thus when the helical track has a left-handed orientation, rotation of the dose-knob in the clockwise direction results in its displacement in the proximal (dose-setting) direction. On the other hand, when helical track has a right-handed orientation, rotation of the dose-knob in the anti-clockwise direction results in its displacement in the proximal (dose-setting) direction. The outer dose-drum also carries on its outer surface, the dose-setting numerals.

The outer and inner dose-drums are locked in assembly by two retaining clips that, in one embodiment, are integral to the distal edge of the inner dose-drum moulding, whereas in another embodiment are integral to the distal edge of the outer dose-drum. An additional component of the dose setting/injection assembly is the thumb pad that is present at the proximal end of the injection device. The thumb pad is free to rotate on a bearing surface at the proximal end of the inner dose-drum. Present on the outer surface of the inner dose-drum, at its proximal end, are sprung ridge teeth that contact with inner mating teeth that are arrayed on the inside of dose-knob on the proximal edge. The sprung ridge teeth and inner mating teeth mate with each other at an angle to the axis of rotation and have a duel function, one of which is that of a bi-directional ratchet that produces tactile and auditory clicks when the outer dose-knob is rotated in order to set a dose. The second function is to provide an axial spring force between the inner dose-drum and the outer dose-drum. Also present on the outer surface of the inner dose-drum, and on its proximal region, are engagement teeth that can lock with corresponding circularly arrayed teeth on the distal edge of the dose-knob to form a dog clutch. The relative location of these two sets of engagement teeth with respect to each other is such that when the thumb pad is depressed, they are interlocked to form a dog clutch. But once the thumb pad is released, the axial spring force between the sprung ridge teeth and the inner mating teeth force the interlock between the latter set of engagement teeth, that form the dog clutch, apart.

The drive-shaft of the piston drive mechanism has an outer threading that mates corresponding internal threading on the piston rod, forming a non-self-locking thread connection. Depending on the orientation of the helical track of the outer threading on the drive-shaft, rotation of the drive-shaft in either the clockwise or anti-clockwise direction drives the piston rod in distal direction. Thus when the threading has a right-handed orientation, rotation of the drive-shaft in the anti-clockwise direction results in the displacement of the piston rod in the distal direction. On the other hand when the threading is that of a left-handed helix, rotation of the drive-shaft in the clockwise direction results in the displacement of the piston rod in the distal direction. Displacement of the piston rod in the distal direction results in the delivery of the fluid. At proximal end of the drive-shaft threading is a collar, the proximal face of which forms a bearing surface with a corresponding inner face of the proximal end of the inner housing-tube. This bearing surface permits the drive-shaft to rotate relative to the inner housing-tube, but restraints it from moving axially in the proximal direction.

In the proximal portion of the drive-shaft, located beyond the drive-shaft collar, is the drive-shaft coupling, which when assembled defines a groove between its distal face and the proximal bearing face of the drive-shaft collar. The distal face of the drive-shaft coupling forms a bearing surface with the outer face of the proximal end of the inner housing-tube. Combination of the drive-shaft collar bearing surface and drive-shaft coupling bearing surface acts to retain its axial position relative to its inner housing tube. The drive-shaft coupling may either be molded as part of the drive-shaft, or it may made as a separate component and then fixed on to the proximal portion of the drive-shaft. In either case the drive-shaft coupling is functionally an integral component of the drive-shaft. In case the drive-shaft coupling is a molded part of the drive-shaft, it comprises two components—ratchet teeth and legs. On the other hand when the drive-shaft coupling is a separately constructed part that is then fixed on to the proximal portion of the drive-shaft, it comprises an additional component, finger clips, in addition to the ratchet teeth and legs. The finger-clips hold in place the drive-shaft coupling to the drive-shaft. The proximal portion of the drive-shaft may have a non-circular cross-section, such as a square, in which case there must be appropriate number of finger clips that grip on to the drive-shaft (for example four clips in case the drive-shaft proximal end has the cross section of the square). The legs of the drive-shaft coupling are coupled with channels that traverse the length of the inner dose-drum on its inner surface. The drive-shaft is thus coupled to the inner dose-drum by means of the legs. This keyed assembly permits axial movement of the inner dose-drum relative to the drive-shaft. The ratchet teeth on the drive-shaft coupling interdigits teeth of a corresponding ratchet clip on the inner housing-tube to form a one-way ratchet. The ratchet teeth and ratchet clip are oriented in such a way that they permit the rotation of the drive-shaft in only one direction, viz. either clockwise or anti-clockwise. The consequence of the legs of the drive-shaft coupling with the inner dose-drum, and the ratchet teeth on the drive-shaft engaging the ratchet clips of the inner-housing-tube is that it results in a one-way coupling between the driving mechanism and the dose-setting assembly. This coupling plays an important role in the functioning of the dose setting, as well as the delivery system of the delivery device of the present invention.

The dose setting and delivery functions of the delivery device of the present invention depend on the relative direction of rotation, clockwise or anti-clockwise, of the outer-dose-drum during dose setting, and the drive-shaft during dose delivery; as well as the restriction of rotation (in either clockwise or anti-clockwise direction) of the drive-shaft by the ratchet teeth and ratchet clip interdigiting. Thus in the design of the fluid delivery device in accordance to the present invention, when the helical track of the outer-housing tube-dose-drum has a left-handed helical orientation, so that rotation of the dose-drum in the clockwise direction results in its displacement in the proximal (dose-setting) direction, then the outer threading of the drive-shaft must have a right-handed helical orientation, so that rotation of the drive-shaft in the anti-clockwise direction results in the displacement of the piston rod in the distal direction. Also in such a design, the relative orientation of the ratchet teeth and ratchet clip inter-digiting is such that, rotation of the drive-shaft is permitted only in the anti-clockwise direction (and not in the clockwise direction). In such an embodiment, when the dose-knob is rotated in a clockwise direction, the dose-drum is rotated and axially displaced in the proximal direction. This in turn displaces the inner dose-drum axially in the proximal direction, thus setting an appropriate dose. When the thumb pad is depressed, the inner dose-drum is forced axially inwards so that the engagement teeth on the proximal outer surface of the inner dose-drum and on the distal edge of the dose-knob get interlocked to form a dog clutch. This results in the locking the inner dose-drum and the outer dose-drum. When this happens, the two dose-drums are in rotational assembly so that they spiral in an anti-clockwise rotation in the distal direction together. This in turn rotates the drive-shaft in an anti-clockwise direction and forces the piston rod forward. The forward movement of the piston rod in turn delivers the appropriate dose of the fluid in the fluid cartridge.

On the other hand, when the helical track of the outer housing-tube-dose-drum has a right-handed helical orientation, so that rotation of the dose-drum in the anti-clockwise direction results in its displacement in the proximal (dose-setting) direction, then the outer threading of the drive-shaft must have a left-handed helical orientation, so that rotation of the drive-shaft in the clockwise direction results in the displacement of the piston rod in the distal direction. In such a design, the orientation of ratchet teeth and ratchet clip inter-digiting is such that, rotation of the drive-shaft is permitted only in the clockwise direction. Hence, in this embodiment of the present invention, when the outer dose-knob is rotated in an anti-clockwise direction, it is rotated and axially displaced in the proximal direction. This in turn displaces the inner dose-drum axially in the proximal direction, thus setting an appropriate dose. When the thumb pad is depressed, the engagement teeth on the proximal outer surface of the inner dose-drum and on the distal edge of the dose-knob get interlocked to form a dog clutch. This results in the locking the inner dose-drum and the outer dose-drum, which then spiral in a clockwise rotation in the distal direction. The drive-shaft in turn rotates in an clockwise direction and forces the piston rod forward. The forward movement of the piston rod delivers the appropriate dose of the fluid in the fluid cartridge.

The medication injection device of the present invention may have a clear window with a lens molded on to the outer housing-tube. This provides clear visibility to the underlying dose-setting numerals that are present on the outer dose-drum along a track parallel to the helical track of the not-locking thread pitch between the outer housing-tube and the outer dose-drum. The size of the said window opening is such that only single dosage numerals are visible at any time.

The above mechanism describes the design of reusable delivery devices, viz. devices in which the empty cartridge can be replaced by a fresh one. The same design can be easily adapted to obtain "disposable" devices that are discarded after a single use. This can be done by joining the distal edge of the inner housing-tube and the proximal edge of the cartridge holder. The crucial difference is that the distal edge of the inner housing-tube is joined with the proximal edge of the cartridge holder to form a single enclosure that on its distal part encloses the fluid cartridge and on its proximal part is the inner housing-tube which encloses the dose-setting and driving mechanisms, and mates with the outer housing-tube by means of the non-locking thread and rib arrangement. In one embodiment, the said two edges are joined by a clip-ridge inter-locking between said edges of the cartridge. In an alternative embodiment, the said edges are joined by chemically bonding or ultrasonically welding together the said edges.

At the distal end of either of the embodiments, the needle is attached after the fluid cartridge has been assembled. The needle hub can be fastened by a mechanical clip, or chemical bonding or ultrasonic welding.

Further, in the disposable devices of the above embodiments, the locking bush is molded out of the distal region of the inner housing-tube, the inner surface of which has protrusion that mates with the longitudinal channels that traverse the length of the outer surface of the piston rod. In one embodiment, the said two edges are joined by a clip-ridge inter-locking between said edges of the cartridge.

We describe below some of the embodiments of the present invention. The various embodiments only serve to illustrate the present invention. It should however be understood that they do not in any way restrict the scope of the invention. It is possible for a person skilled in the art to make obvious modifications to various components of a delivery device, for example, changes to cartridge holder or to dose drum, plunger, etc. to arrive at a similarly functional design and the instant invention is deemed encompass all such modifications.

Description of Specific Embodiments

The invention is described in detail with references to the drawing. The delivery devices described in the following embodiments have the overall shape and appearance of a pen, and have been described, in these embodiments, as fluid delivery pens.

BRIEF DESCRIPTION OF THE DRAWINGS

FIGS. 1, 2, 3 4, 5, 6 and 7 show the reusable fluid delivery pen, in accordance to the present invention.

FIG. 1 shows the delivery pen in its fully assembled and capped form.

FIG. 2A is a sectional view along the line that sections through the center of the dose window of FIG. 1. FIGS. 2A and B also shows the positions of the plunger before (position 10) and after (position 10d) the fluid has been completely ejected. FIGS. 3, 4, 5 and 6 shows the assembled delivery pen, in accordance with the present invention, in which certain layers of the pen are "made transparent", or not shown, in order to expose the underlying components.

In FIG. 3 the cartridge holder and the outer housing-tube is made transparent.

In FIGS. 4A, B and C the outer housing-tube is not shown, and the outer dose-drum has been made transparent.

In FIG. 5 the outer housing-tube is not shown. This figure shows the delivery pen when the cartridge-holder has not yet been assembled on to the housing.

In FIG. 6A, the outer housing-tube, outer dose-drum, inner dose-drum, the inner housing-tube and the piston rod cap are not shown. In FIG. 6B in addition to the outer housing-tube, outer dose-drum, inner dose-drum and the inner housing-tube, the hollow piston rod are not shown, in order to reveal the threading of the drive-shaft. In FIGS. 6C and D the outer housing-tube, outer dose-drum, inner dose-drum are not shown. FIGS. 1, 2, 3, 4, 5 and 6 are embodiments in which the inner and outer housing-tubes are ultrasonically welded together.

DETAIL DESCRIPTION OF THE DRAWINGS

Figure 1:
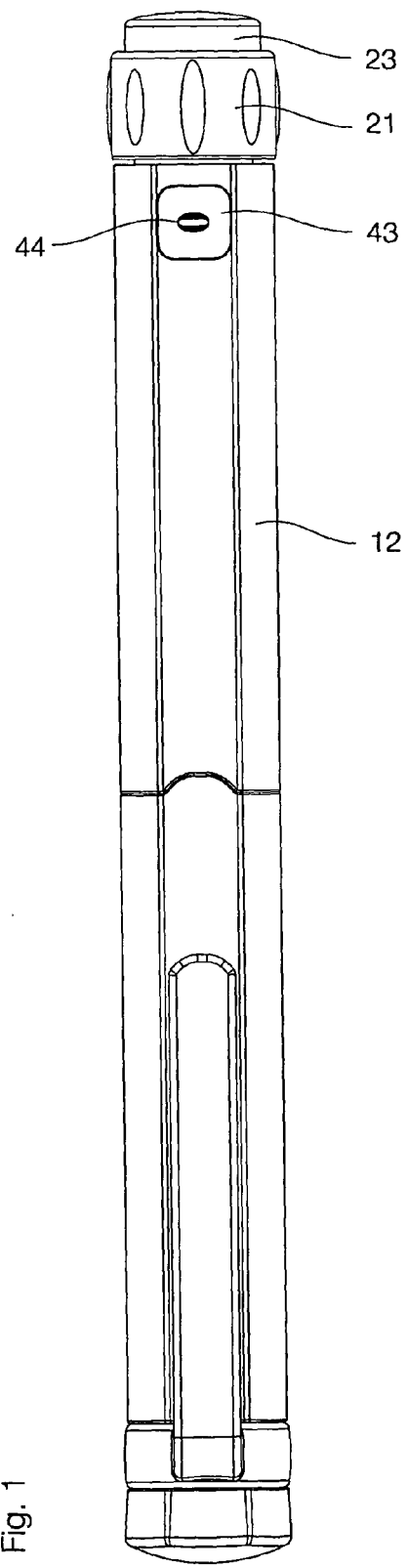
Figure 2A:
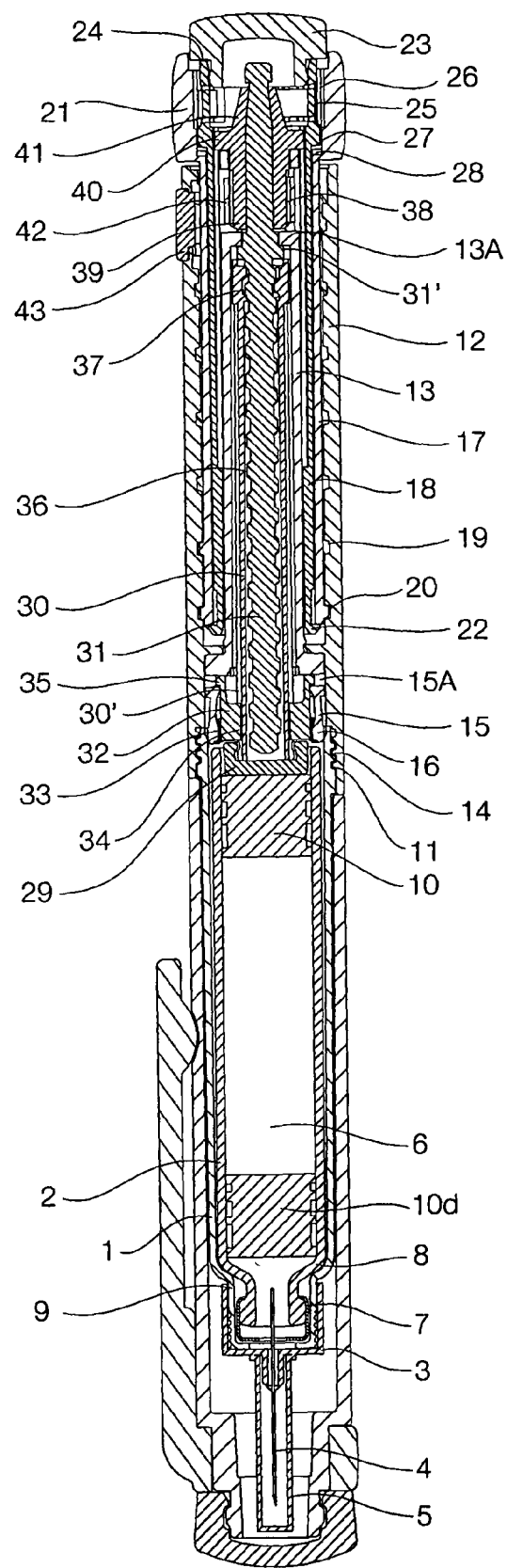
FIGS. 2A and B shows sectional views of the same along different lines in FIG. 1.
Figure 2B:
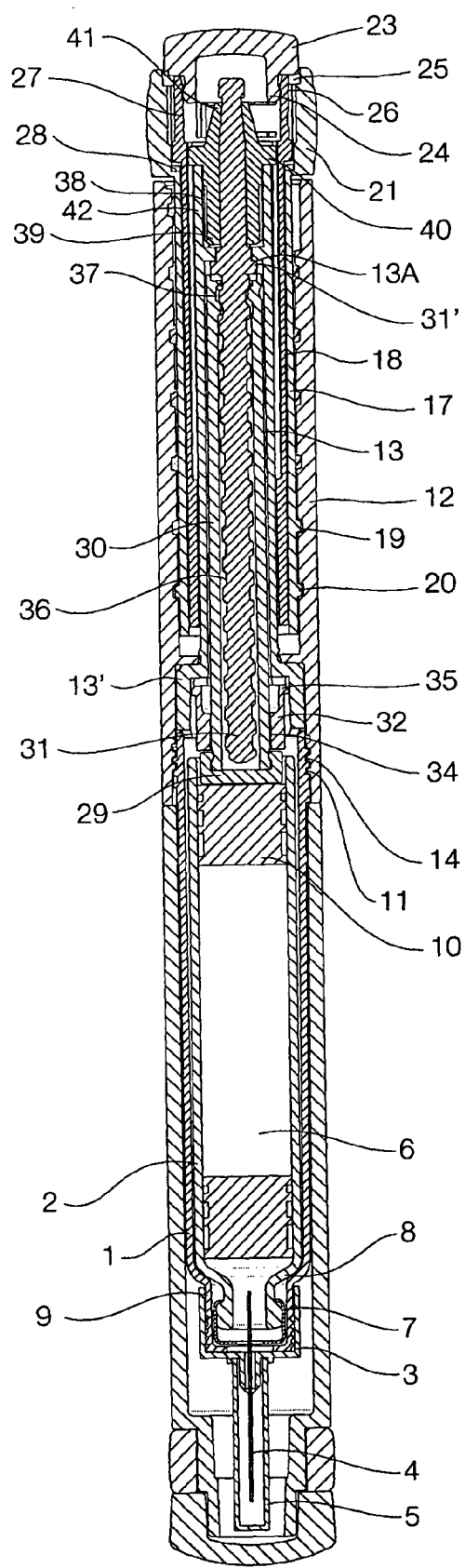
FIG. 2B is a section at 90° with respect to FIG. 2A.
Figure 3:
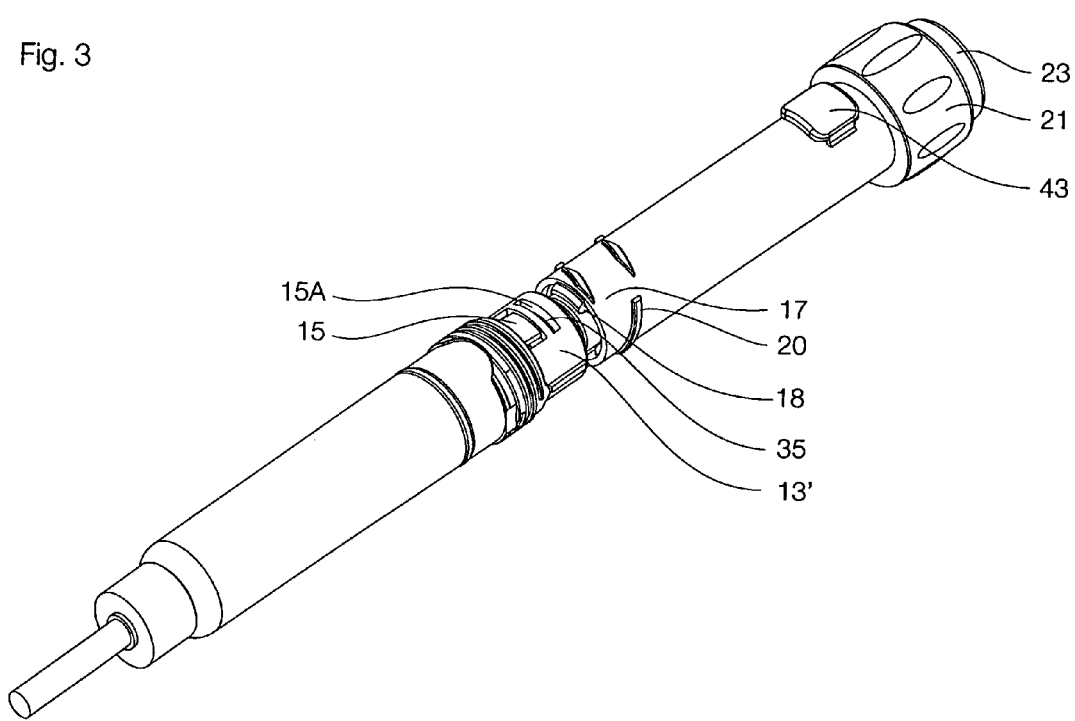
Figure 4:
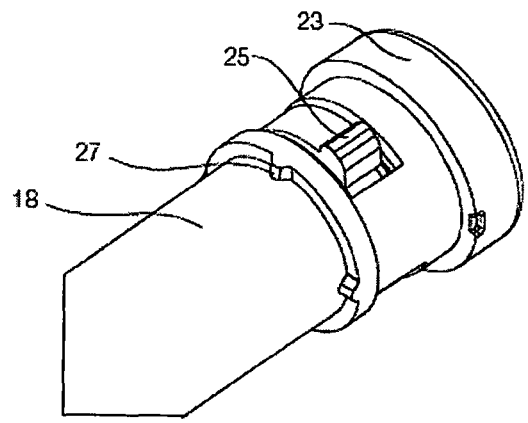
Figure 4:
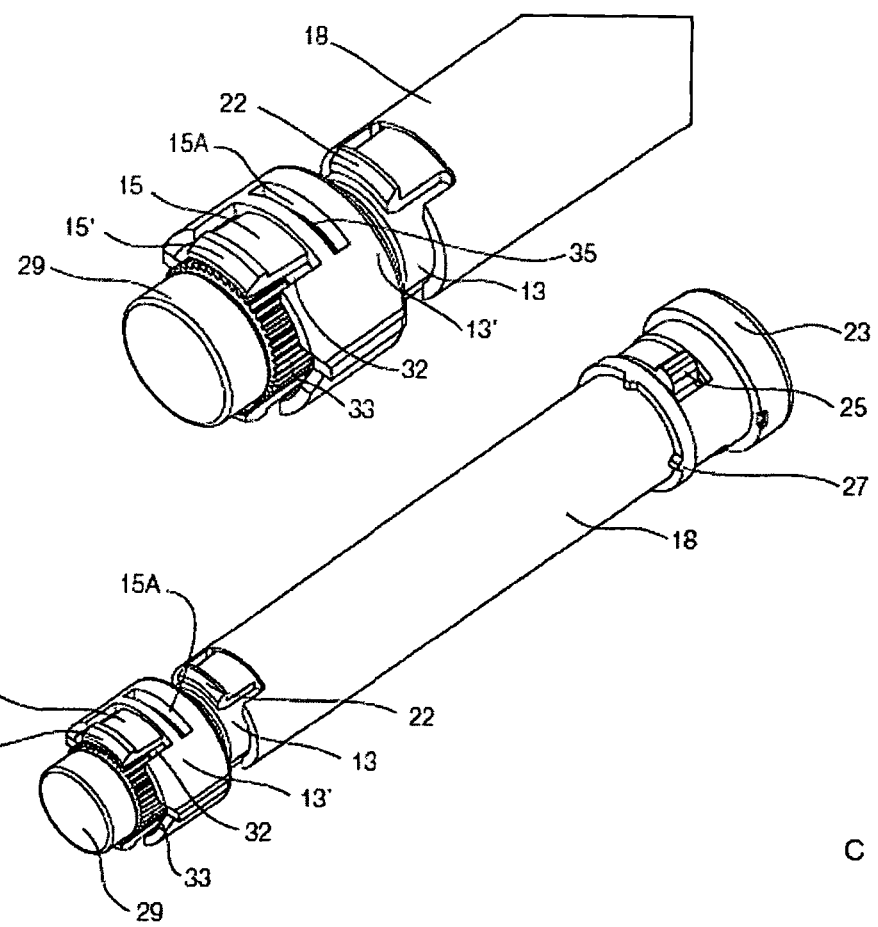
Figure 5:
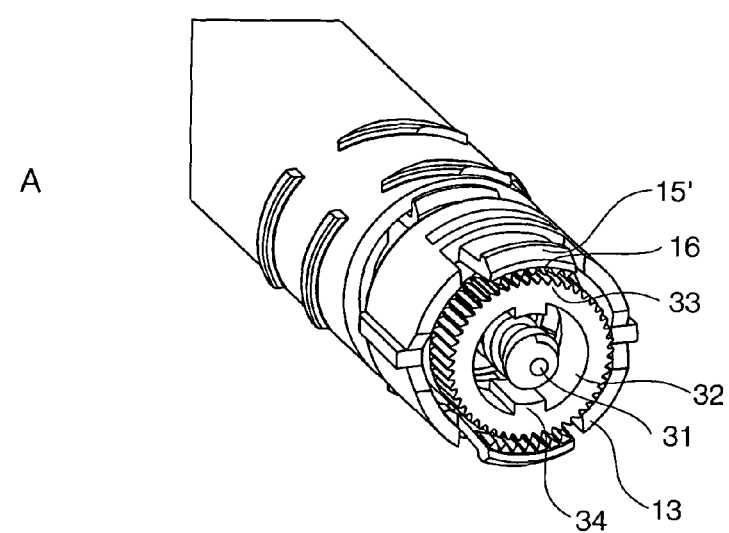
Figure 5:
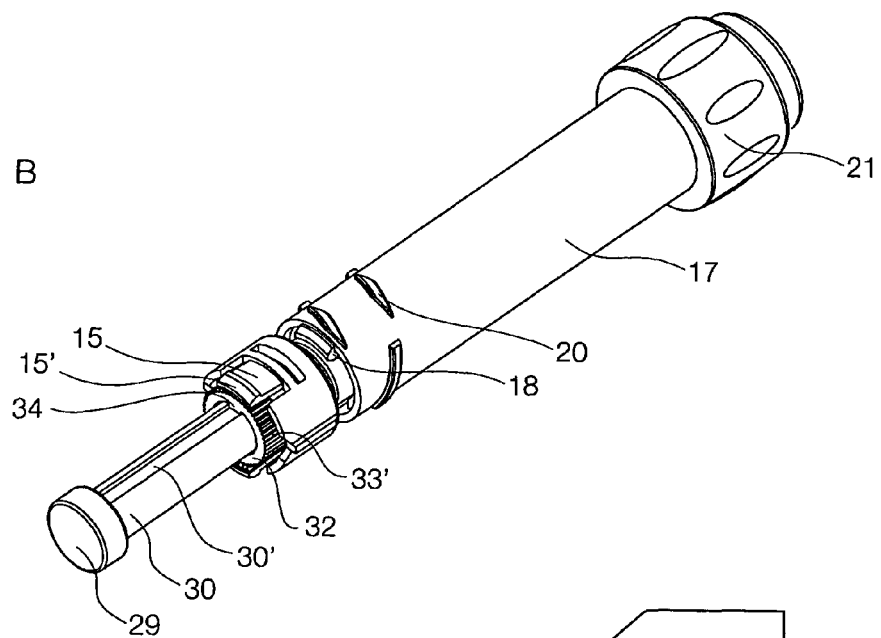
Figure 5:
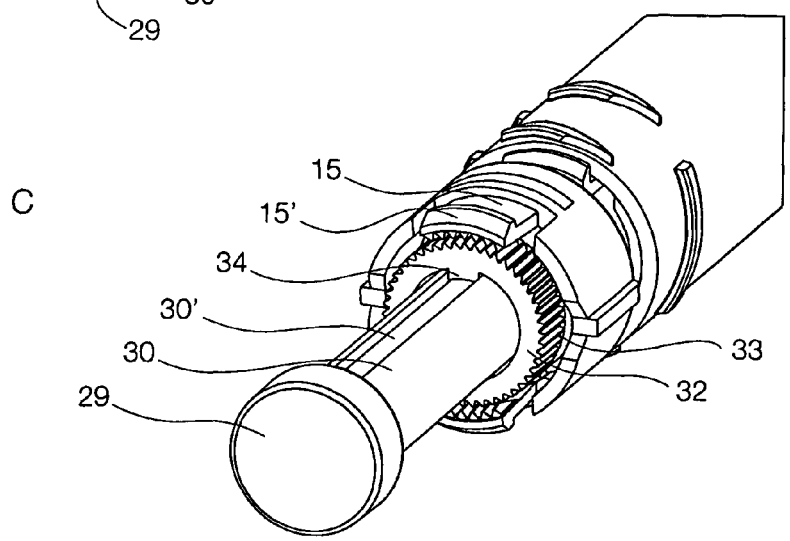
Figure 6:
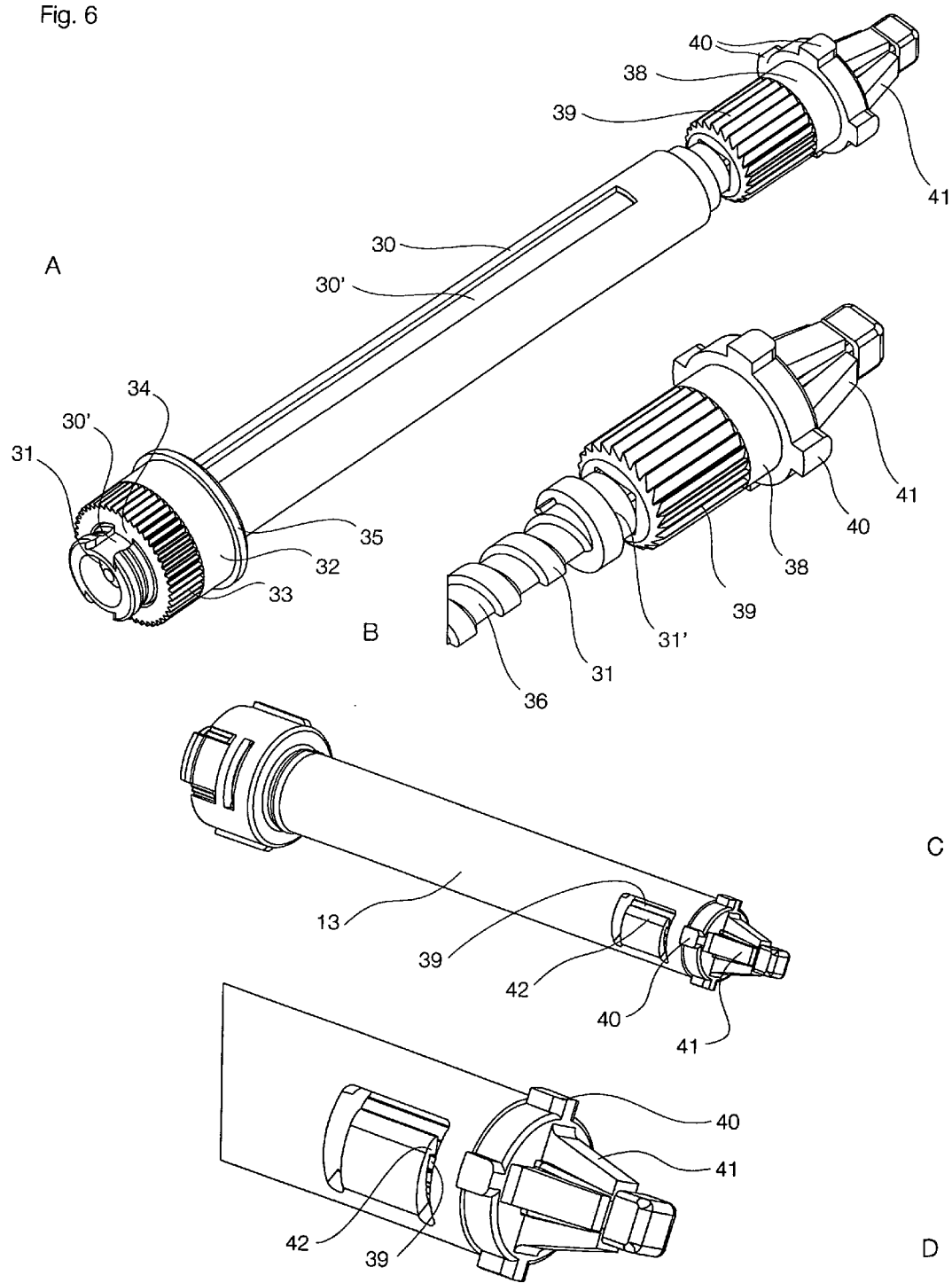

FIG. 1 shows the delivery pen in its fully assembled and capped form. This Figure that exemplifies that embodiment of the present invention, wherein the delivery device has the overall shape and appearance of a pen. Thus, FIG. 1 exemplifies the outer housing tube 12, which includes the thumb pad 23. The dose control knob 21 is used to vary or control the amount of fluid administered. The window or viewing portion of the outer housing 23 permits the user to view the numerical settings 44 which present or correspond to the dosage controls or settings.

With reference to the embodiments shown in FIGS. 2-6, the fluid delivery pen can be described as comprising two regions. The distal half of the pen comprises the cartridge holder 1 for holding the fluid containing cartridge 2. On the distal end of the cartridge holder 1 is mounted the needle hub 3, that carries the needle 4. The portion of the needle 4 that projects out of the cartridge holder 1 is, in turn, enclosed by a protective cap 5. The proximal end of the needle communicates with the content 6 of the cartridge. The cartridge 2, comprising the fluid 6, is loaded inside the cartridge holder 1 such that the head 7 and neck 8 of the cartridge is snugly fixed into the neck region 9 of the cartridge holder 1. The distal end of the cartridge is sealed, but the proximal portion of the needle traverses through it in order to communicate with cartridge content 6. The proximal end of the cartridge is enclosed by an airtight, but movable, plunger 10, 10d (10d being the plunger after all the available medication has been completely ejected). The outer surface of the cartridge holder, on its proximal end, has helical threads 11.

The proximal half of the pen comprises the pen housing which encloses the dose-setting and driving mechanisms. The pen housing comprises two concentrically arranged housing-tubes—the outer housing-tube 12 and the inner housing-tube 13. On the inner side of the outer housing, at its distal end, are helical threads 14. The cartridge holder 1, containing the medication cartridge 2, is mounted into the housing by screwing it into the outer housing-tube 12 by means of mating threads, 11, 14, on the outer surface of the proximal end of the cartridge holder and on the inner surface of the distal end of the outer housing-tube respectively. Concentrically arranged inside the outer housing-tube 12 is the inner housing-tube 13. Portions of distal portion of the inner housing-tube 13, diametrically opposite each other, are molded as two sprung-clips 15 that are deflected inward when the cartridge holder 1 is mounted into outer-housing-tube 12. The two sprung-clips 15 comprise an inner-toothed surface 16. The inner housing-tube 13 is joined to the outer housing-tubes 12 by ultrasonically welding the non-clip distal region 13' of the inner housing-tube 13 to the inner wall of the outer housing-tube 12. The inner housing-tube 13 encloses the piston drive apparatus, while two concentrically arranged dose-drums—the outer dose-drum 17 and the inner dose-drum 18—are placed between the inner 13 and outer 12 housing-tubes. A not-self-locking thread connection is formed between the inner side of the outer housing-tube 12 and the outer dose-drum 17 by a helical thread 19 on the inner side of the outer housing-tube 12 that engages helical ribs 20 present on the surface of outer dose-drum 17. The proximal portion of the dose-drums project out of the proximal end of the outer housing-tube 12. Thus the proximal portion of the outer dose-drum—the dose-knob 21—is amenable to rotation by hand. Thus when the dose-knob 21 is rotated, the outer dose-drum 17 is both rotated and axially displaced relative to the housing. The helical thread 19 on inner side of the outer housing-tube 12 has a left-handed orientation. Hence when the dose-knob 21 is rotated in the clockwise direction it results in the displacement of the dose-drum in the proximal (dose-setting) direction. The outer dose-drum 17 also carries on its outer surface, and along a track parallel to the above helical track, the dose-setting numerals.

The outer 17 and inner 18 dose-drums are locked in assembly by two retaining clips 22 that are integral to the distal edge of the inner dose-drum molding. The two retaining clips 22 deflect inwards when the inner dose-drum is being assembled into the outer dose-drum, and spring out when the inner dose-drum is in its correctly assembled position. In the assembled pen the inner housing is located down the bore of the inner dose-drum, thereby preventing the retaining clips 22 from deflecting inwards, thus ensuring that the inner and outer dose-drums remain locked together.

A thumb pad 23 is present at the proximal end of the injection device. The thumb pad 23 is free to rotate on a bearing surface 24 at the proximal end of the inner dose-drum 18. On the outer surface of the inner dose-drum 18, close to its proximal end, are sprung ridge teeth 25 that contact with mating teeth 26 that are arrayed along the inner circumference of dose-knob 21 on the proximal edge. The said sprung ridge teeth 25 and inner mating teeth 26 mate with each other at an angle to the axis of rotation, and thereby have a duel function. One of the functions is that of a bi-directional ratchet which produces tactile and auditory clicks when the dose-knob is rotated to set the dose. The second function is to provide an axial spring force between the inner dose-drum and the outer dose-drum. Present on the outer surface of the inner dose-drum 18, and on its proximal region, are engagement teeth 27 that can lock with corresponding circularly arrayed teeth 28 on the distal edge of the dose-knob 21 to form a dog clutch. The relative location of these two sets of engagement teeth 27, 28 with respect to each other is such that, when the thumb pad 23 is depressed, the said teeth 27, 28 are interlocked to form a dog clutch. But once the thumb pad 23 is released, the axial spring force between the sprung ridge teeth and inner mating teeth, 25 and 26, force the interlock between the latter engagement teeth 27, 28 apart.

The piston drive apparatus comprises a piston rod cap 29, a hollow piston rod 30 and a drive-shaft 31. The piston rod cap 29 is free to rotate on a bearing surface with the piston rod 30, and directly contacts the cartridge plunger 10, 10d. The drive-shaft 31 is located, at least partially, inside the piston rod 30. A flexible locking bush 32, comprising an outer tooth surface 33, is placed between the distal end of the piston rod 30 and the inner housing-tube 13. When the cartridge holder 1 is assembled into the pen, the two inner housing-tube sprung-clips 15 are deflected inwards, so that the teeth 16 on the inner side of the sprung-clip 15 engage the outer surface teeth 33 of the locking bush 32, preventing the locking bush 32 from rotating. The inner surface of the locking bush 32 has protrusions 34 which mate with the longitudinal channels 30' that traverse the length of outer surface of the piston rod 30. Hence when the cartridge-holder 1 is assembled into the pen, the piston rod 30 is prevented from rotating. On the other hand when the cartridge holder is removed, the teeth 16, 33 on the sprung-clips 15 and on the locking bush 32 respectively become disengaged, thereby allowing rotation of the locking bush 32 and the piston rod 30. The proximal edge of the locking bush 32 has a ridge 35 that is retained within a corresponding groove 15A formed beyond the proximal edge of the two sprung-clips 15 of the inner housing-tube. The distal edge of the two sprung-clips 15 has a raised ramp 15' that locks into a corresponding champfer on the inner side of the proximal edge of the cartridge-holder pushing the sprung-clips progressively inwards as the cartridge holder is screwed into the outer housing tube. The drive-shaft 31 has an outer threading 36 that mates with the corresponding internal threading 37 on the piston rod, forming a non-self locking thread connection. The helical thread 36 on the outer surface of the drive-shaft 31 has a right-handed orientation, so that when the drive-shaft 31 is rotated in the anti-clockwise direction, the piston rod 30 is displaced in the distal direction relative to the drive shaft. This displacement of the piston rod in the distal direction pushes the cartridge plunger 10d in the distal direction ejecting the medication. In addition, at the proximal end of the drive shaft threading 36 there is a collar 31'. The proximal face of the drive-shaft collar 31' forms a bearing surface with the corresponding inner face of the proximal end 13A of the inner housing tube. This bearing surface permits the drive-shaft to rotate relative to the inner housing tube, but restraints the drive-shaft from moving axially in the proximal direction.

The proximal portion of the drive-shaft 31 comprises the drive-shaft coupling 38 which is located beyond the drive-shaft collar 31', and which when assembled defines a groove between its distal face and the proximal bearing face of the drive-shaft collar 31'. The distal face of the drive-shaft coupling forms a bearing surface with the outer face of the proximal end 13A of the inner housing tube. Combination of the drive-shaft collar 31' bearing surface and drive-shaft coupling bearing surface acts to retain the drive-shaft in its axial position relative to its inner housing tube.

The drive-shaft coupling 38 is molded as a separate component and then fixed on to the proximal portion of the drive-shaft. However the drive-shaft coupling 38 is functionally an integral component of the drive-shaft. The drive-shaft coupling 38 comprises three components—a ratchet teeth 39, legs 40 and finger clips 41. Four finger-clips 41 hold in place the drive-shaft coupling 38 to the proximal portion of the drive-shaft 31 which has the cross-section of a square. The legs 40 of the drive-shaft coupling 38 are coupled with channels that traverse the length of the inner dose-drum 18 on its inner surface. The drive-shaft 31 is thus coupled to the inner dose-drum 18 by means of the legs 40. This keyed assembly permits axial movement of the inner dose-drum 18 relative to the drive-shaft 31. The ratchet teeth 39 on the drive-shaft coupling 38 interdigit the teeth of a corresponding ratchet clips 42 on the inner housing-tube 13 to form a one way ratchet. The interdigiting ratchet teeth and ratchet clip 39, 42 are oriented in such a way that they permit the rotation of the drive-shaft 31 in only the anti-clockwise direction. The consequence of the legs 40 of the drive-shaft coupling 38 coupling with the inner dose-drum 18, and the ratchet teeth 39 on the drive-shaft coupling 38 engaging the ratchet clips 42 of the inner housing-tube 13 is that it results in a one-way coupling between the driving mechanism and the dose-setting assembly, whereby the piston rod can only be displaced in the distal direction, when the pen is fully assembled. This coupling is key to the functioning of the dose setting, as well as the delivery system of the delivery device of the present invention.

A clear window with a lens 43 is molded on the outer housing-tube 12. This provides clear visibility to the underlying dose-setting numerals 44, the dose-scale, that are present on the outer dose-drum 12 along a track parallel to the helical track 19 of the not-locking thread between the outer housing-tube 12 and the outer dose-drum 18. The size of the said window opening 43 is such that only single dosage numerals 44 are visible at any time.

To set the dose the outer dose-knob 21 is rotated in a clockwise direction. This results in the rotation and axial displacement of the outer dose-drum 17 in the proximal direction, thus setting an appropriate dose, which appears in the dose window 43. This in turn displaces the inner dose-drum 18 axially in the proximal direction. The size of the set dose can be seen on the portion of the dose-scale that is presented in the window. If an excess dose has been set the dose-knob 21 can be rotated in the anti-clockwise direction until the number corresponding to the required dose-size appears in the window 43. To deliver the set dose the thumb pad 23 is depressed. The inner dose-drum 18 is then forced axially inwards, so that the engagement teeth 27 on the proximal region of the outer surface of the inner dose-drum 18, and the circularly arrayed teeth 28 on the distal edge of the dose-knob 21 become interlocked, thus locking together the inner dose-drum 13 and the outer dose-drum 12. When this happens, the two dose setting drums 17, 18 are in rotational assembly so that they spiral in an anti-clockwise rotation in the distal direction all the way back to the "zero setting". This in turn rotates the drive-shaft 31 in an anti-clockwise direction through the legs 40 of the drive shaft coupling 38 and forces the piston rod 30 forward. The forward movement of the piston rod delivers the appropriate dose of the fluid from the fluid cartridge 2. In another embodiment, in the case of the not-self-locking thread connection that is formed between the inner side of the outer housing-tube and the outer dose-drum by the helical thread-helical rib engagement, the helical thread is present on the outer surface of outer dose-drum, while the helical ribs are present on the inner side of the outer housing-tube. The helical thread present on the surface of outer dose-drum has a left-handed helix orientation. Hence in this embodiment as well, when the dose-knob is rotated in the clock-wise direction to set a dose, the outer dose-drum is rotated and axially displaced relative to the housing.

In another embodiment of the present invention, in the case of the not-self-locking thread connection formed between the inner side of the outer housing-tube and the outer dose-drum by the helical thread-helical rib engagement, the helical thread of the helical track has a right-handed orientation, so that rotation of the dose-drum in the anti-clockwise direction results in its displacement in the proximal (dose-setting) direction. In a sub-embodiment of this embodiment, the helical thread is present on the inner side of the outer housing-tube, while the helical ribs are present on the outer dose-drum. In another sub-embodiment, the helical thread is present on the surface of outer dose-drum, while the helical ribs are present on the inner side of the outer housing-tube. In either sub-embodiments, the outer threading of the drive-shaft has a left-handed orientation, so that rotation of the drive-shaft in the clockwise direction results in the displacement of the piston rod in the distal direction. Furthermore in such a design, the orientation of the ratchet teeth and ratchet clip interdigiting is such that, rotation of the drive-shaft is permitted only in the clockwise direction. Hence in these embodiments the dose is set by rotating the dose-knob in an anti-clockwise direction, so that the dose-drums are rotated and axially displaced in the proximal direction. When the thumb pad is depressed, the engagement teeth on the proximal outer surface of the inner dose-drum and on the distal edge of the dose-knob get interlocked to form a dog clutch. This results in the locking the inner dose-drum and the outer dose-drum, which then travel in a clockwise rotation towards the distal direction. The drive-shaft in turn rotates in a clockwise direction and forces the piston rod forward. The forward movement of the piston rod delivers the appropriate dose of the fluid.

Figure 7A:
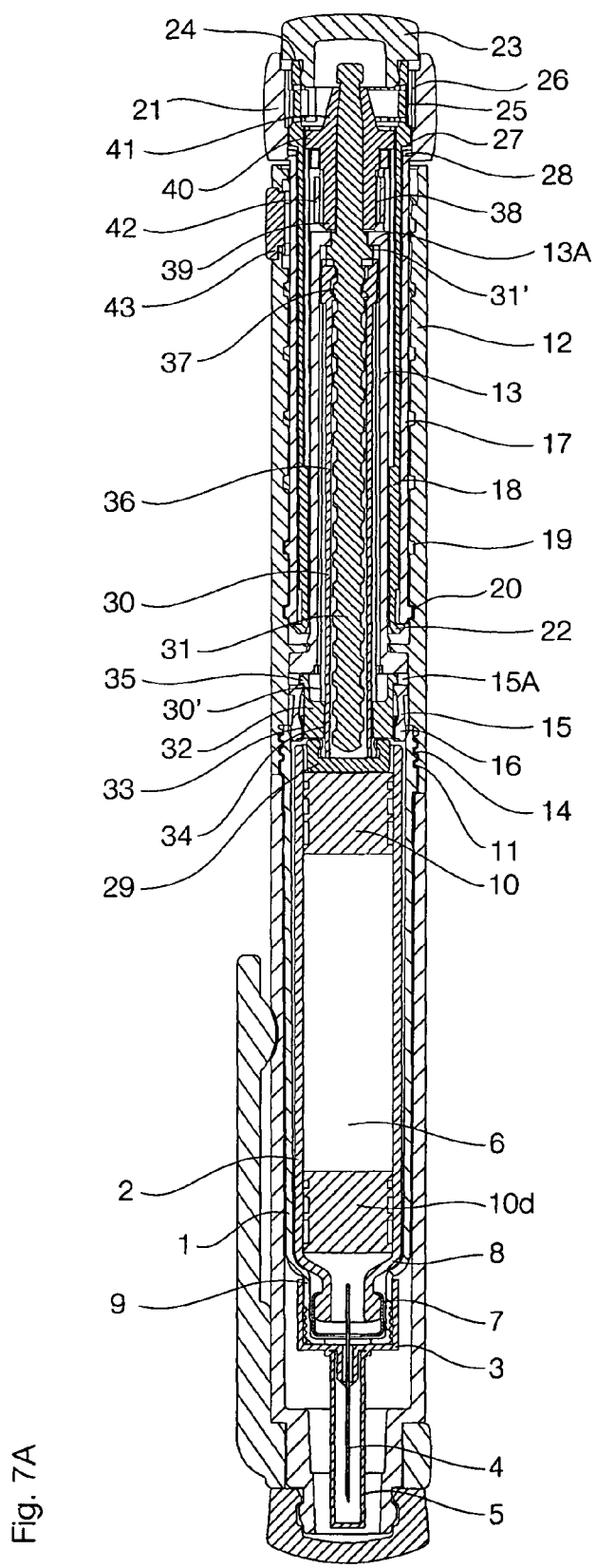
FIGS. 7A and B are embodiments in which the inner and outer housing-tubes are joined be means of thread-screw connections.
Figure 7B:
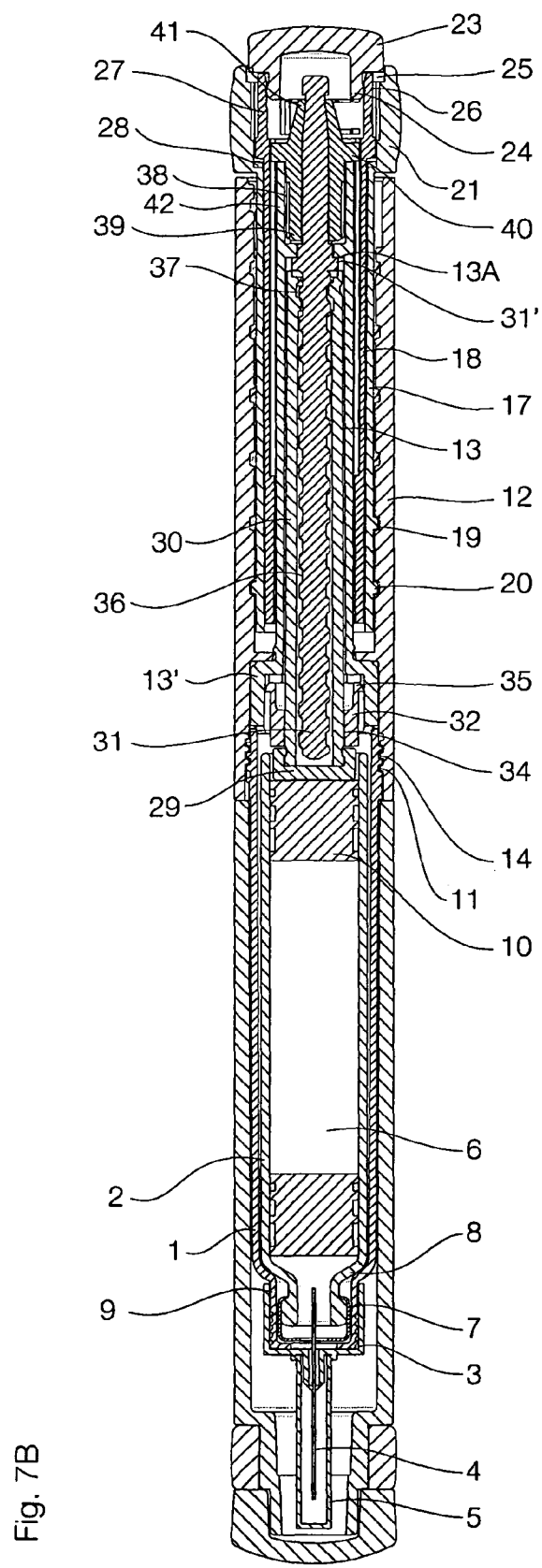

In another embodiment of the present invention, the housing-tubes are joined by means of a thread-screw connection (FIGS. 7A and B). In this embodiment, the inner housing-tube is joined to the outer housing-tubes by means of a thread-screw arrangement (13' in FIG. 7A) between the non-clip distal region of the inner housing-tube to the inner wall of the outer housing-tube.

In another embodiment of the present invention, the outer and inner dose-drums are locked in assembly by two clips that are integral to the distal edge of the outer dose-drum moulding.

In yet another embodiment of the present invention, the drive-shaft coupling is molded as part of the drive-shaft, so that the finger clips are not required.

Figure 8A:
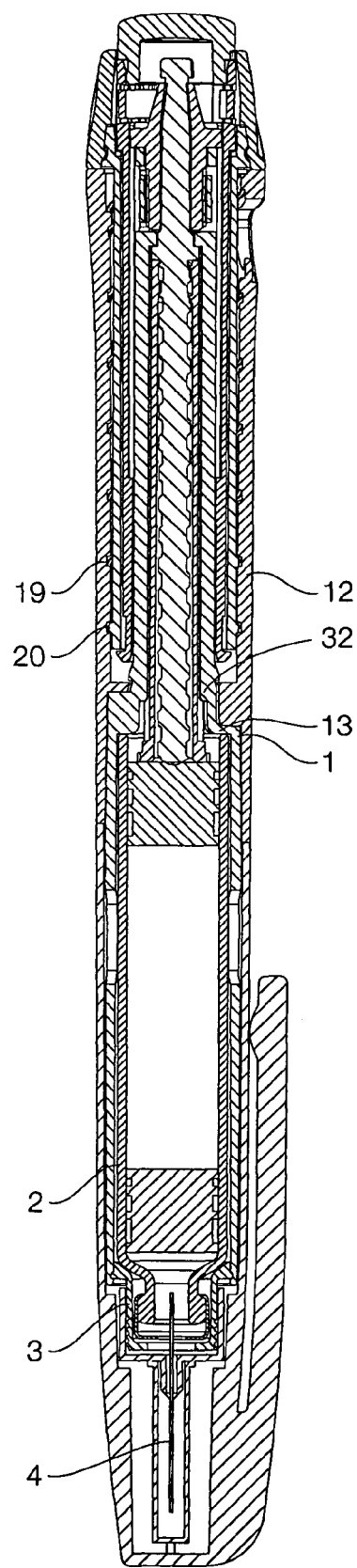
FIGS. 8A and 8B describe the design of disposable delivery devices, viz. those which are discarded once the cartridge 2 is empty.
Figure 8B:
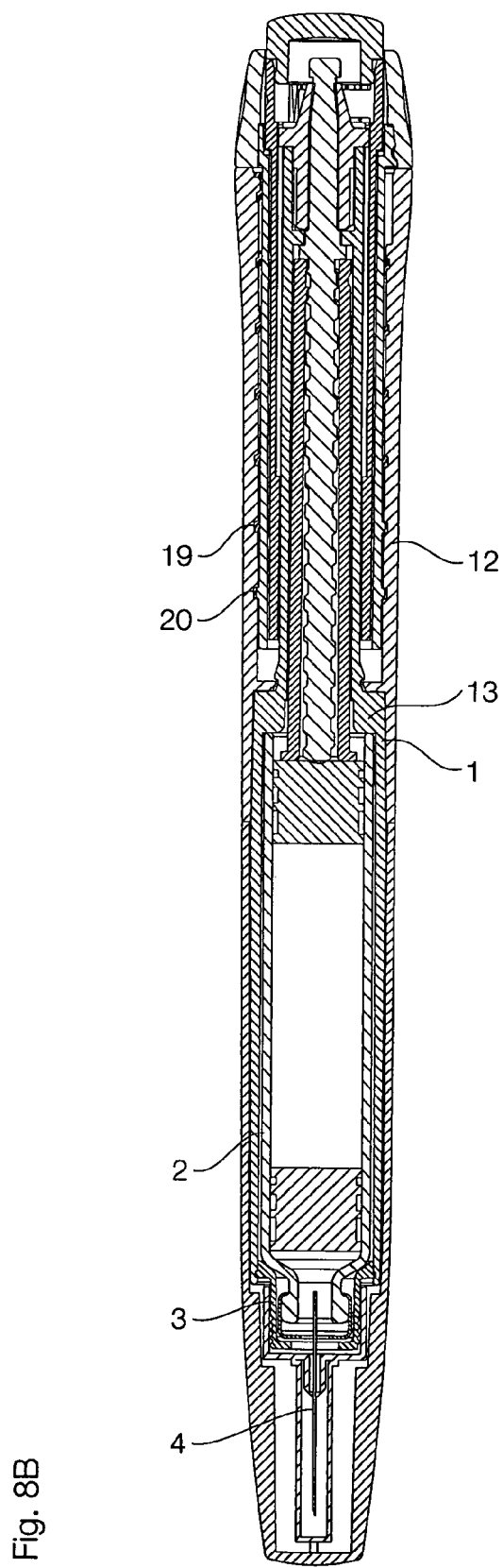

FIGS. 8A and 8B describe the design of disposable delivery devices, viz. those which are discarded once the cartridge 2 is empty. The same design features described in all the above embodiments are incorporated in the disposable devices as well. The crucial difference is that the distal edge of the inner housing-tube 13 is joined with the proximal edge of the cartridge holder 1 to form a single enclosure that on its distal part encloses the fluid containing cartridge 2 and on its proximal part is the inner housing-tube 13 which encloses the dose-setting and driving mechanisms, and mates with the outer housing-tube 12 by means of the non-locking thread 19 and rib 20 arrangement. In one embodiment, the said two edges are joined by a clip-ridge inter-locking between said edges of the cartridge. In an alternative embodiment the said edges are joined by chemically bonding or ultrasonically welding together the said edges. At the distal end of either embodiments, the needle 4 is attached after the fluid containing cartridge 2 has been assembled. The needle hub 3 can be fastened by a mechanical clip, chemical bonding or ultrasonic welding.

Further, in the disposable devices of the above embodiments, the locking bush (32) is molded out of the distal region of the inner housing-tube, the inner surface of which has protrusion which mate with the longitudinal channels that traverse the length of the outer surface of the piston rod.

We claim:

1. A delivery device that comprises:
   a fluid cartridge holder comprising a cartridge containing fluid,
   a housing,
   a piston drive mechanism situated within the housing and comprising a hollow piston rod and a drive-shaft,
   which hollow piston rod has an internal thread on at least a portion of its inner surface and a non-circular outer section,
   and which drive-shaft has an external thread which mates with the internal thread of the hollow piston rod forming a thread connection and being axially restrained in the proximal direction relative to the housing, a piston drive mechanism for rotating the drive-shaft such that upon activation of the driving mechanism the piston rod is forced to move axially in the distal direction causing ejection of the fluid from the cartridge, the delivery device further characterized in that the internal threads on the hollow piston rod and the external threads on the drive shaft are not exposed when the cartridge holder is removed.

2. A delivery device according to claim 1 wherein the piston rod is prevented from rotating by a locking bush with an inner profile which mates with the non-circular outer section of the piston rod, and wherein the housing comprises a concentrically arranged outer housing-tube and an inner housing-tube.

3. A delivery device according to claim 2 wherein the piston drive mechanism is connected to the housing via a one way ratchet such that the piston rod is prevented from moving axially.

4. A delivery device according to claim 3 wherein the piston drive mechanism is connected to the housing via a one way ratchet such that the piston rod is prevented from moving axially in the proximal direction.

5. A delivery device according to claim 4 wherein the drive-shaft is connected to the housing via a one way ratchet such that the drive shaft is prevented from rotating in the direction which would result in movement of the piston rod axially in the proximal direction.

6. A delivery device according to claim 1 wherein the housing comprises a concentrically arranged outer housing-tube and an inner housing-tube.

7. A delivery device according to claim 6 wherein the piston drive mechanism is located within the inner housing-tube.

8. A delivery device according to claim 7 wherein the piston drive mechanism is connected to the inner housing-tube via a one way ratchet such that the piston rod is prevented from moving axially.

9. A delivery device according to claim 8 wherein the piston drive mechanism is connected to the inner housing-tube via a one way ratchet such that the piston rod is prevented from moving axially in the proximal direction.

10. A delivery device according to claim 9 wherein the drive-shaft is connected to the inner housing-tube via a one way ratchet such that the drive-shaft is prevented from rotating in the direction which would result in movement of the piston axially.

11. A delivery device according to claim 10 wherein the drive-shaft is connected to the inner housing-tube via a one way ratchet such that the drive-shaft is prevented from rotating in the direction which would result in movement of the piston axially in the proximal direction.

12. A delivery device according to claim 11 wherein the drive-shaft comprises ratchet teeth that inter digit correspondingly located teeth on the inner housing-tube to form the one-way ratchet.

13. A delivery device according to claim 12 wherein the ratchet teeth are present on the drive-shaft.

14. A delivery device according to claim 13 wherein the ratchet teeth are present on the proximal region of the drive-shaft.

15. A delivery device according to claim 2 wherein the locking bush is located between the piston rod and the inner housing-tube.

16. A delivery device according to claim 15 wherein the locking bush is located between the distal end of the piston rod and the inner housing-tube.

17. A delivery device according to claim 16 in which the inner profile of the locking bush are protrusions that mate with longitudinal channels that traverse the length of the non-circular outer portion of the piston rod, thereby preventing the piston rod from rotating.

18. A delivery device according to claim 17 in which the locking bush further comprises an outer toothed surface.

19. A delivery device according to claim 18 wherein the portions of the inner housing-tube are further molded as two sprung clips.

20. A delivery device according to claim 19 wherein the portions of the distal portion of the inner housing-tube are further molded as two sprung clips.

21. A delivery device according to claim 20 wherein the sprung clips further comprise an inner toothed surface that engage with the outer toothed surface of the locking bush.

22. A delivery device according to claim 1 further comprising:
a dose setting means comprising,
an outer dose-drum located within the housing, wherein the outer dose-drum and the housing are mated by a non locking helical thread-rib arrangement,
an inner dose-drum rotationally connected to the drive-shaft and located within the outer dose-drum and capable of being rotationally connected or disconnected from the outer dose-drum, so that when rotationally disconnected, the outer dose-drum can be rotated spirally outwards in the proximal direction to set a dose, or spirally inwards to set a lower dose; and when rotationally connected to the outer dose-drum will transmit the rotation of the outer dose-drum to the drive-shaft forcing the piston rod out.

23. A delivery device according to claim 22 further comprising:
a dose setting means comprising,
an outer dose-drum located within the housing, wherein the outer dose-drum and the housing are mated by a non locking helical thread-rib arrangement,
an inner dose-drum rotationally connected to the drive-shaft and located within the outer dose-drum and capable of being rotationally connected or disconnected from the outer dose-drum, so that when rotationally disconnected, the outer dose-drum can be rotated spirally outwards in the proximal direction to set a dose, or spirally inwards to set a lower dose; and when rotationally connected to the outer dose-drum will transmit the rotation of the outer dose-drum to the drive-shaft forcing the piston rod out in the distal direction.

24. A delivery device according to claim 23 wherein the outer dose-drum and the inner dose-drum are located between the outer housing-tube and inner housing-tube.

25. A delivery device according to claim 24 in which the outer dose-drum and the outer housing-tube are mated by a helical thread-rib arrangement.

26. A delivery device according to claim 25 wherein,
when the piston drive mechanism is activated, the inner dose-drum, that is rotationally connected to the drive-shaft, gets rotationally connected with the outer dose-drum, and will transmit the rotation of the outer dose-drum to the drive-shaft which in turn forces the piston rod to move axially;
and when the driving mechanism is not activated, the inner dose-drum, that is rotationally connected to the drive-shaft, gets rotationally disconnected from the outer dose-drum, so that the outer dose-drum can be rotated spirally outwards to set a dose, and spirally inwards to set a lower dose.

27. A delivery device according to claim 26 wherein,
when the piston drive mechanism is activated, the inner dose-drum, that is rotationally connected to the drive shaft, gets rotationally connected with the outer dose-drum, and will transmit the rotation of the outer dose-drum to the drive-shaft which in turn forces the piston rod to move axially in the distal direction;
and when the driving mechanism is not activated, the inner dose-drum, that is rotationally connected to the drive-shaft, gets rotationally disconnected from the outer dose-drum, so that the outer dose-drum can be rotated spirally outwards in the proximal direction to set a dose, and spirally inwards to set a lower dose.

28. A delivery device according to claim 27 wherein the inner surface of the inner dose-drum is rotationally connected to the drive-shaft.

29. A delivery device according to claim 28 wherein the inner surface of the inner dose-drum is rotationally connected to legs present on the drive-shaft.

30. A delivery device according to claim 29 wherein the inner surface of the inner dose-drum is rotationally connected to legs present on the proximal portion of the drive-shaft.

31. A delivery device according to claim 30 wherein the said legs are connected to channels that traverse the inner surface of the inner dose-drum.

32. A delivery device according to claim 22 wherein the piston drive mechanism is activated by depressing a thumb pad.

33. A delivery device according to claim 32 wherein,
when the piston drive mechanism is activated, the inner dose-drum, that is rotationally connected to the drive-shaft by legs, gets rotationally connected with the outer dose-drum, and will transmit the rotation of the outer dose-drum to the drive-shaft which in turn forces the piston rod to move axially,
and when the driving mechanism is inactivated, the inner dose-drum, that is rotationally connected to the drive-shaft, gets rotationally disconnected from the outer dose-drum, so that the outer dose-drum can be rotated spirally outwards to set a dose, and spirally inwards to set a lower dose.

34. A delivery device according to claim 33 wherein,
when the piston drive mechanism is activated, the inner dose-drum, that is rotationally connected to the drive-shaft by legs, gets rotationally connected with the outer dose-drum, and will transmit the rotation of the outer dose-drum to the drive-shaft which in turn forces the piston rod to move axially in the distal direction;
and when the driving mechanism is inactivated, the inner dose-drum, that is rotationally connected to the drive-shaft, gets rotationally disconnected from the outer dose-drum, so that the outer dose-drum can be rotated spirally outwards in the proximal direction to set a dose, and spirally inwards to set a lower dose.

35. A delivery device according to claim 34 that further comprises, on the outer surface of the inner dose-drum, sprung ridge teeth that contact with inner mating teeth that are arrayed along the inner circumference of the outer dose-drum such that the said sprung ridge teeth and inner mating teeth mate with each other at an angle to the axis of rotation.

36. A delivery device according to claim 35 that further comprises, on the outer surface of the inner dose-drum, close to its proximal end, sprung ridge teeth that contact with inner mating teeth that are arrayed along the inner circumference of the outer dose-drum on the proximal end, such that the said sprung ridge teeth and inner mating teeth mate with each other at an angle to the axis of rotation.

37. A delivery device according to claim 36 that further comprises,
on the outer surface of the inner dose-drum but located distal to the sprung ridge teeth, engagement teeth,
on the outer dose-drum, circularly arrayed teeth, the location being distal with respect to that of the engagement teeth,
the relative location of the engagement teeth and the circularly arrayed teeth with respect to each other being such that, when the thumb pad is depressed, the said engagement teeth and circularly arrayed teeth get interlocked, and when the thumb pad is released, the axial spring force between the sprung ridge teeth and the mating teeth force the interlock between the engagement teeth and the circularly arrayed teeth apart.

38. A delivery device according to claim 37 that further comprises,
on the outer surface of the inner dose-drum on its proximal region, but located distal to the sprung ridge teeth, engagement teeth,
on the proximal region of the outer dose-drum, circularly arrayed teeth, the location being distal with respect to that of the engagement teeth,
the relative location of the engagement teeth and the circularly arrayed teeth with respect to each other being such that, when the thumb pad is depressed, the said engagement teeth and circularly arrayed teeth get interlocked, and when the thumb pad is released, the axial spring force between the sprung ridge teeth and the mating teeth force the interlock between the engagement teeth and the circularly arrayed teeth apart.

39. A deliver device according to claim 38 wherein when the piston drive mechanism is activated, the engagement teeth and the circularly arrayed teeth are interlocked, and the inner dose-drum is rotationally connected with the outer dose-drum, and transmits the rotation of the outer dose-drum to the drive-shaft which in turn forces the piston rod to move axially, and
when the drive mechanism is inactivated, the interlock between the engagement teeth and the circularly arrayed teeth are parted, and inner dose-drum is rotationally disconnected with the outer dose-drum, so that the outer dose-drum can be rotated spirally outwards to set a dose, and spirally inwards to set a lower dose.

40. A deliver device according to claim 39 wherein when the piston drive mechanism is activated, the engagement teeth and the circularly arrayed teeth are interlocked, and the inner dose-drum is rotationally connected with the outer dose-drum, and will transmit the rotation of the outer dose-drum to the drive-shaft which in turn forces the piston rod to move axially in the distal direction, and
when the drive mechanism is inactivated, the interlock between the engagement teeth and the circularly arrayed teeth are parted, and inner dose-drum is rotationally disconnected with the outer dose-drum, so that the outer dose-drum can be rotated spirally outwards in the proximal direction to set a dose, and spirally inwards to set a lower dose.

41. A delivery device according to claim 40 wherein the drive mechanism comprises a thumb pad.

42. A delivery device according to claim 41 wherein the thumb pad is present at the inner dose-drum.

43. A delivery device according to claim 42 wherein the thumb pad is present at the proximal end of the inner dose-drum.

44. A delivery device according to claim 43 wherein the thumb pad is free to rotate on a bearing surface at the proximal end of the inner dose-drum.

45. A delivery device according to claim 44 wherein the drive mechanism is activated by depressing the thumb pad.

* * * * *